United States Patent [19]

Rendenbach-Mueller et al.

[11] Patent Number: 5,401,762
[45] Date of Patent: Mar. 28, 1995

[54] AMINOALKYL-SUBSTITUTED THIAZOLIN-2-ONES, THE PREPARATION AND USE THEREOF

[75] Inventors: Beatrice Rendenbach-Mueller, Waldsee; Hans-Juergen Teschendorf, Dudenhofen; Liliane Unger, Ludwigshafen, all of Germany

[73] Assignee: BASF Aktiengesellschaft, Ludwigshafen, Germany

[21] Appl. No.: 162,116

[22] PCT Filed: May 12, 1992

[86] PCT No.: PCT/EP92/01039

§ 371 Date: Dec. 13, 1993

§ 102(e) Date: Dec. 13, 1993

[87] PCT Pub. No.: WO92/22539

PCT Pub. Date: Dec. 23, 1992

[30] Foreign Application Priority Data

Jun. 15, 1991 [DE] Germany .................. 41 19 757.7

[51] Int. Cl.⁶ .................. C07D 277/34; C07D 417/06; A01K 31/425

[52] U.S. Cl. .................. 514/369; 514/252; 514/326; 514/333; 544/367; 546/209; 546/280; 548/189

[58] Field of Search .................. 548/189; 544/367; 546/209, 280; 54/369, 252, 326, 333

[56] References Cited

FOREIGN PATENT DOCUMENTS 2521104  11/1975  Germany .

*Primary Examiner*—Robert Gerstl
*Attorney, Agent, or Firm*—Keil & Weinkauf

[57] ABSTRACT

Aminoalkyl-substituted thiazolin-2-one derivatives of the formula

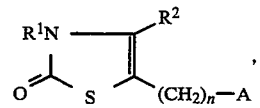

where n and A have the meanings stated in the description, and the preparation thereof are described. The compounds are suitable for controlling diseases.

4 Claims, No Drawings

AMINOALKYL-SUBSTITUTED THIAZOLIN-2-ONES, THE PREPARATION AND USE THEREOF

The present invention relates to aminoalkyl-substituted thiazolin-2-ones, the preparation thereof and the use thereof for controlling diseases.

BE 829 071 describes 4-aryl-5-aminoalkylthiazolin-2-ones with pharmacological activities.

We have now found that aminoalkyl-substituted thiazolin-2-ones of the formula I

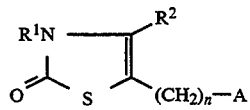

where
$R^1$ is H or $C_1$-$C_5$-alkyl,
$R^2$ is H or $C_1$-$C_5$-alkyl,
n is an integer from 1 to 6,
A is

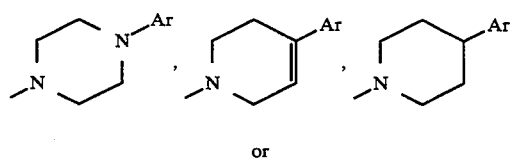

or

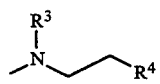

where Ar is phenyl which is unsubstituted or monosubstituted by $C_1$-$C_5$-alkyl, $C_1$-$C_5$-alkoxy, halogen, nitro, hydroxyl, $C_1$-$C_5$-alkylthio, trifluoromethyl or cyano, or is pyridyl, pyrimidinyl or thienyl, $R^3$ is H or $C_1$-$C_5$-alkyl, and $R^4$ is phenyl which is unsubstituted or monosubstituted by $C_1$-$C_5$-alkyl, $C_1$-$C_5$-alkoxy, halogen, hydroxyl or trifluoromethyl, or is thienyl, and their tautomers and salts of these compounds with physiologically tolerated acids have interesting pharmacological properties.

In the formula I, $R^1$ is preferably H, $R^2$ is preferably $CH_3$, n is preferably 2, 3 or 4, and A is preferably

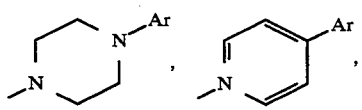

where Ar is phenyl, pyridyl or pyrimidinyl, or

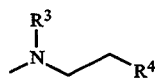

where $R^3$ is $C_1$-$C_3$-alkyl and $R^4$ is phenyl or thienyl.

The tautomers derived from the compounds of the formula I have the formula Ia

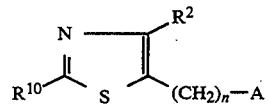

The compounds of the formula I can be prepared by
a) reacting an ω-X-alkyl-substituted thiazolin-2-one of the formula II

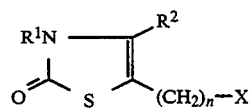

where $R^1$, $R^2$ and n are as defined above, and X is a leaving group such as chlorine, bromine or $R^5SO_2O$—[$R^5$=$C_1$-$C_4$-alkyl or phenyl which is unsubstituted or substituted by $C_1$-$C_3$-alkyl or halogen], or, when $R^1$ is H, a tautomer of this compound, with an amine of the formula III

HA        III, where A has the stated meanings, or
b) reacting an α-halo ketone of the formula IV

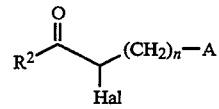

where $R^2$, $R^3$, A and n are as defined above, and Hal is chlorine, bromine or iodine, or a hydrohalide of this compound, with a thiocarbamate of the formula V

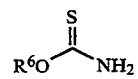

where $R^6$ is $C_1$-$C_5$-alkyl, or with a tautomer of this compound, or
c) alkylating a compound of the formula VI

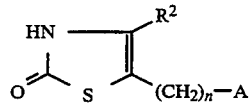

where $R^2$, A and n are as defined above, with an alkylating reagent $R^1$—X (X=Cl, Br, $R^5SO_2O$—) or $R^1_2SO_4$, where appropriate converting the resulting compounds into their salts with physiologically tolerated acids.

The reaction in process a) takes place in the melt, if required also in the presence of a solvent, e.g. ethanol, butanol, ethyl acetate, tetrahydrofuran, dimethylformamide, dimethoxyethane toluene or xylene, at from room temperature to the boiling point of the solvent, preferably in the presence of a base such as sodium methylate, sodium ethylate, sodium hydride, sodium carbonate, potassium carbonate, or of an amine, e.g. pyridine. It is also possible where appropriate for the amine component IV in excess to act as reagent, base and solvent.

The crude product is isolated in a conventional way, e.g. by filtration, removal of the solvent by distillation, or extraction from the reaction mixture. The resulting compound is purified in a conventional way, for example by recrystallization from a solvent, chromatography or conversion into an acid addition compound.

The thiazolin-2-ones of the formula II used as starting materials can be prepared, for example, by halogenation of an ω-X-substituted ketone of the formula VII

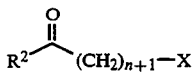

where $R^2$, n and X have the stated meanings, and subsequently reacting the halo ketone with a thiocarbamate of the formula V.

The reactions in process b) are preferably carried out in a solvent at from room temperature to the boiling point of the solvent, in the presence or absence of an acid acceptor. Examples of solvents which can be used are aliphatic alcohols, dimethylformamide, glacial acetic acid, water or a solvent mixture, and of acid acceptors are inorganic bases such as sodium or potassium carbonate or tertiary organic bases such as triethylamine or pyridine. If used in excess, the latter can also act as solvent.

The α-halo ketones of the formula IV used as starting materials are obtained by halogenating the corresponding ketones of the formula VIII

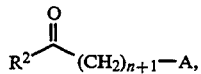

where $R^2$, A and n have the stated meanings. The compounds of the formula IV obtained in this way need no further purification.

The reaction in process c) is carried out by methods known from the literature for the alkylation of secondary amides. It is possible to melt the components together in the absence of a solvent. However, the reaction is also possible in the presence of an inert solvent, e.g. an aromatic hydrocarbon such as toluene or xylene, an ether such as tetrahydrofuran or dioxane, a ketone such as acetone or butanone, an amide such as dimethylformamide or N-methylpyrrolidone, a nitrile such as acetonitrile, a halohydrocarbon or dimethyl sulfoxide. It is beneficial to add a base, e.g. sodium methylate, sodium ethylate, sodium hydride, a carbonate, a hydroxide or a tertiary amine such as triethylamine or pyridine.

The resulting compounds according to the invention are, where appropriate, converted into their addition salts with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid and benzoic acid. Others are to be found in Fortschritte der Arzneimittelforschung, Vol. 10, pp. 224 et seq., Birkhäuser Verlag, Basel and Stuttgart, 1966.

The acid addition salts are usually obtained in a conventional way by mixing the free base or solutions thereof with the appropriate acid or solutions thereof in an organic solvent, for example a lower alcohol such as methanol, ethanol or propanol, a halohydrocarbon such as methylene chloride, an ether such as methyl t-butyl ether or diisopropyl ether, a ketone such as acetone or butanone or an ester such as ethyl acetate. It is also possible to use mixtures of the said solvents to improve crystallization. In addition, pharmaceutically acceptable aqueous solutions of acid addition compounds of the compounds I according to the invention can be prepared by dissolving the free bases in an aqueous acid solution.

The compounds according to the invention are suitable for controlling diseases, especially for treating disorders of the central nervous system (e.g. parkinsonism, schizophrenia) and high blood pressure. They have, in particular, valuable properties as dopamine receptors, in some cases with selectivity for presynaptic dopamine receptors, or as dopamine antagonists. The compounds of the formula I show affinity for the dopamine receptor in receptor binding assays; they inhibit motility in mice (measured in cages with a photoelectric beam) and influence the pivoting behavior of rats with unilateral 6-hydroxydopamine lesions of the substantia nigra (Brain Research 24, (1970) 485–493).

The effects of the novel compounds can be shown in the receptor binding assay as follows:

Striata from rats (Sprague Dawley, Charles River) were homogenized immediately after removal in 0.32M sucrose solution (0° C.). The homogenate was filtered through gauze, the filtrate was centrifuged at 1000 xg (5 min at 4° C.) and the resulting supernatant was centrifuged at 40000 xg (4° C., 10 min). The residue (membranes) was taken up in incubation buffer (50 mM tris-HCl, 1 mM $MgCl_2$ and 0.1% ascorbic acid, pH 7.4) and incubated at 37° C. for 20 min. The residue was subsequently washed 2× with incubation buffer by resuspension and recentrifugation. The membranes were frozen in portions in liquid nitrogen.

The assay mixtures (1 ml) were composed of membranes (380 μg of protein), 1 nM $^3$H-ADTN (NEN, Dreieich Germany, specific radioactivity 1.4 TBq/mmol) and 0.1 μM SCH 23390 (total binding) or a) with the addition of 50 nM spiperone (non-specific binding) or b) with-test substance. The mixtures were prepared in triplicate.

After the incubation (40 min at 25° C.) the mixtures were filtered through glass fiber filters (Whatman GF/B) and briefly washed with ice-cold washing buffer (Tris-HCl pH 7.4). The radioactivity retained on the filters was determined by liquid scintillation counting. The non-specific binding comprised about 40–50% of the total binding.

The evaluation of the competition plots and the determination of the dissociation constant took place by iterative non-linear regression analysis based on the "ligand" program (Muson and Rodbard: Anal. Biochem. 107 (1980) 220).

| Affinity of the test substances for the dopamine $D_2$ receptor | |
|---|---|
| Example | Ki (nM) |
| 1 | 8 |
| 2 | 15 |
| 7 | 12 |
| 10 | 25 |
| 12 | 6 |
| 13 | 45 |
| 14 | 6 |
| 17 | 40 |

The compounds according to the invention can be administered orally or parenterally (subcutaneously, intravenously, intramuscularly, intraperitoneally) in a conventional way. Administration can also take place through the nasopharyngeal space using vapors or sprays.

The dosage depends on the age, condition and weight of the patient and on the mode of administration. The dose of active substance is, as a rule, about 10–500 mg per patient and day on oral administration and about 1–100 mg per patient and day on parenteral administration.

The novel compounds can be used in the conventional solid or liquid pharmaceutical forms, e.g. as uncoated (film-coated) coated tablets, capsules, powders, granules, suppositories, solutions or sprays. These are produced in a conventional way. The active substances can be processed with conventional pharmaceutical aids such as tablet binders, fillers, preservatives, tablet disintegrants, flow regulators, plasticizers, wetting agents, dispersants, emulsifiers, solvents, retarding agents, antioxidants and/or propellant gases (cf. H. Sucker et al.: Pharmazeutische Technologie, Thieme-Verlag, Stuttgart, 1978). The pharmaceutical forms obtained in this way normally contain the active substance in an amount of from 1 to 99% by weight.

The following examples illustrate the invention:

EXAMPLE 1

4-Methyl-5-[3-(1,2,3,6-tetrahydro-4-phenylpyridyl)-propyl]-thiazolin-2-one hydrochloride 4.5 g of 5-(3-chloropropyl)-4-methylthiazolin-2-one, 4.6 g of 1,2,3,6-tetrahydro-4-phenylpyridine hydrochloride, 2.5 g of sodium carbonate and a spatula tip of sodium iodide were refluxed in 10 ml of butanol for 10 h. After cooling, the solvent was removed, the residue was partitioned in methyl t-butyl ether/water, and the organic phase was separated off, washed with water and concentrated. The residue was taken up in 2N HCl and the solution was extracted with methylene chloride.

The aqueous phase was adjusted to pH 8 with 2N NaOH and extracted with methyl t-butyl ether. The combined organic phases were dried and concentrated, the residue was dissolved in a little ethanol and ethereal HCl was added. The solid which precipitated after addition of methyl t-butyl ether was filtered off with suction and dried under reduced pressure.

Yield: 2.96 g (36%) Melting point 203°–205° C.

The following were prepared as in Example 1:

2. 4-Methyl-5-[3-(4-pyrid-2-ylpiperazinyl)propyl]-thiazolin-2-one dihydrochloride
 Yield: 23% Melting point 244° C. (decomposition)
3. 4-Methyl-5-[3-(N-phenethyl-N-n-propylamino)-propyl]-thiazolin-2-one fumarate
 Yield: 26% Melting point 110° C.
4. 4-Methyl-5-[3-(4-phenylpiperazinyl)propyl]thiazolin-2-one hydrochloride
 Yield: 23% Melting point 233° C.
5. 4-Methyl-5-[3-(N-thien-2-ylethyl-N-n-propylamino)-propyl]thiazolin-2-one tartrate
 Yield: 52% Melting point 80° C.
6. 4-methyl-5-[3-(4-phenylpiperidinyl)propyl]thiazolin-2-one hydrochloride
 Yield: 38% Melting point 203° C.
7. 4-Methyl-5-[3-(4-pyrimidin-2-ylpiperazinyl)propyl]-thiazolin-2-one dihydrochloride
 Yield: 41% Melting point 245° C.
8. 4-Methyl-5-[3-(4-(3-methoxyphenyl)piperazinyl)-propyl]thiazolin-2-one hydrochloride
 Yield: 40% Melting point 195° C.
9. 4-Methyl-5-[3-(4-(4-chlorophenyl)-1,2,3,6-tetrahydropyridyl)propyl]thiazolin-2-one hydrochloride
 Yield: 37% Melting point 250° C.
10. 4-Methyl-5-[3-(4-(2-ethylphenyl)piperazinyl)-propyl]thiazolin-2-one dihydrochloride
 Yield: 25% Melting point 230° C.
11. 4-Methyl-5-[3-(4-(4-fluorophenyl)-1,2,3,6-tetrahydropyridyl)]thiazolin-2-one hydrochloride
 Yield: 30% Melting point 239°–240° C.
12. 4-Methyl-5-[3-(4-(2-methylthiophenyl)piperazinyl)-propyl]thiazolin-2-one hydrochloride
 Yield: 46% Melting point 248°–249° C.
13. 4-Methyl-5-[3-(4-(3-trifluoromethylphenyl)-piperazinyl)propyl]thiazolin-2-one hydrochloride
 Yield: 19% Melting point 217°–218° C.
14. 4-Methyl-5-[3-(4-(2-ethoxyphenyl)piperazinyl)-propyl]thiazolin-2-one dihydrochloride
 Yield: 31% Melting point 219° C.
15. 4-Methyl-5-[3-(4-(3-chlorophenyl)piperazinyl)-propyl]thiazolin-2-one hydrochloride
 Yield: 17% Melting point 212° C. (decomposition)
16. 4-Methyl-5-[3-(4-(2-cyanophenyl)piperazinyl)-propyl]thiazolin-2-one hydrochloride
 Yield: 25% Melting point 257° C. (decomposition)

EXAMPLE 17

3,4-Dimethyl-5-[3-(4-phenylpiperazinyl)propyl]thiazolin-2-one dihydrochloride 5 g of 4-methyl-5-[3-(4-phenylpiperazinyl)propyl]-thiazolin-2-one, 3.3 g of potassium carbonate and 0.1 g of 18-crown-6 were heated at 60° C. in dimethylformamide for 30 min. Subsequently 2.7 g of methyl iodide were added dropwise, and the mixture was refluxed for 3 h. After cooling, water was added, the mixture was extracted three times with methyl t-butyl ether, and the organic phases were washed with water, dried and concentrated. The residue was dissolved in ethanol, and ethereal HCl was added. The solid which crystallized out on cooling was filtered off with suction and dried.

Yield: 3.3 g (51%) Melting point 222° C.

Examples of pharmaceutical forms:

A) Tablets of the following composition are made in a tableting machine in a conventional way.
 40 mg of substance of Example 1
 120 mg of corn starch
 13.5 mg of gelatin
 45 mg of lactose
 2.25 mg of Aerosil® (chemically pure silica in submicroscopically fine distribution)
 6.75 mg of potato starch (as 6% paste)

B)
 20 mg of substance of Example 4
 60 mg of core composition
 60 mg of coating composition The core composition comprises 9 parts of corn starch, 3 parts of lactose and 1 part of 60:40-vinylpyrrolidone/vinyl acetate copolymer. The coating composition comprises 5 parts of sucrose, 2 parts of corn starch, 2 parts of calcium carbonate and 1 part of talc. The coated tablets produced in this way are subsequently provided with an enteric coating.

c) 10 g of substance of Example 2 are dissolved in 5000 ml of water with the addition of NaCl and adjusted to pH 6.0 with 0.1N NaOH to produce a solution isotonic with blood. 1 ml portions of this solution are introduced into ampoules and sterilized.

We claim:

1. An aminoalkyl-substituted thiazolin-2-one of the formula I

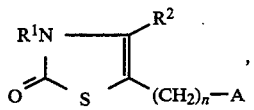

where
R¹ is H or $C_1$-$C_5$-alkyl,
R² is H or $C_1$-$C_5$-alkyl,
n is an integer from 1 to 6,
A is

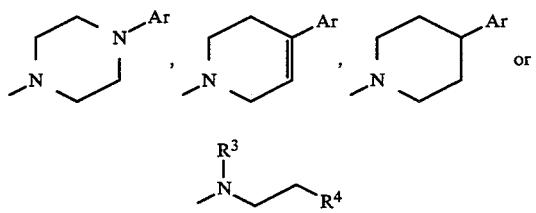

where Ar is phenyl which is unsubstituted or monosubstituted by $C_1$-$C_5$-alkyl, $C_1$-$C_5$-alkoxy, halogen, nitro, hydroxyl, $C_1$-$C_5$-alkylthio, trifluoromethyl or cyano, or is pyridyl, pyrimidinyl or thienyl, R³ is H or $C_1$-$C_5$-alkyl, and R⁴ is phenyl which is unsubstituted or monosubstituted by $C_1$-$C_5$-alkyl, $C_1C_5$-alkoxy, halogen, hydroxyl or trifluoromethyl, or is thienyl, and its tautomers and salts of this compounds with physiologically tolerated acids.

2. The aminoalkyl-substituted thiazolin-2-one compound of formula I, as defined in claim 1, wherein R¹ is H; R² is $CH_3$; n is 2, 3, or 4; and A is

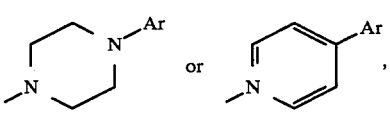

where Ar is phenyl, pyridyl or pyrimidinyl or

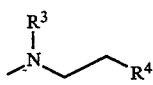

where R³ is $C_1$-$C_3$-alkyl and R⁴ is phenyl or thienyl.

3. A method for controlling high blood pressure, Parkinson's disease and schizophrenia, which comprises administering to a patient in need thereof an effective amount of an aminoalkyl-substituted thiazolin-2-one of the formula I as defined in claim 1.

4. A pharmaceutical composition for treating high blood pressure, Parkinson's disease and schizophrenia, which comprises an aminoalkyl-substituted thiazolin-2-one of the formula I as defined in claim 1 and pharmaceutically acceptable carriers and/or additives.

* * * * *